(12) United States Patent
Shah

(10) Patent No.: US 9,040,471 B2
(45) Date of Patent: May 26, 2015

(54) COMPRESSED GAS AEROSOL COMPOSITION COMPRISING A NON-IONIC SURFACTANT IN A STEEL CAN

(71) Applicant: S. C. Johnson & Son, Inc., Racine, WI (US)

(72) Inventor: Bhaveshkumar Shah, Kenosha, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 14/555,767

(22) Filed: Nov. 28, 2014

(65) Prior Publication Data

US 2015/0083824 A1  Mar. 26, 2015

Related U.S. Application Data

(63) Continuation of application No. 13/422,096, filed on Mar. 16, 2012, now Pat. No. 8,927,474.

(51) Int. Cl.
| | |
|---|---|
| *C11D 1/835* | (2006.01) |
| *C11D 3/18* | (2006.01) |
| *C11D 7/24* | (2006.01) |
| *B05B 9/01* | (2006.01) |
| *B05B 15/00* | (2006.01) |

(52) U.S. Cl.
CPC .. *B05B 9/01* (2013.01); *B05B 15/00* (2013.01)

(58) Field of Classification Search
CPC .......... C11D 1/835; C11D 3/18; C11D 3/048; C11D 3/0073; C11D 3/08; C11D 7/24; C11D 7/5027; C11D 17/0043
See application file for complete search history.

(56) References Cited

U.S. PATENT DOCUMENTS

| | | | | |
|---|---|---|---|---|
| 4,199,622 | A * | 4/1980 | Kokumai et al. | 427/239 |
| 4,358,493 | A * | 11/1982 | Ohtsuki et al. | 428/34.2 |
| 4,683,263 | A * | 7/1987 | Taira et al. | 525/57 |
| 4,773,558 | A * | 9/1988 | Taira et al. | 220/270 |
| 6,943,140 | B2 * | 9/2005 | Ashton et al. | 510/278 |
| 2002/0085988 | A1 * | 7/2002 | Nambu | 424/70.19 |
| 2003/0215417 | A1 * | 11/2003 | Uchiyama et al. | 424/76.2 |
| 2004/0248994 | A1 * | 12/2004 | De Dominicis et al. | 516/6 |
| 2009/0257973 | A1 * | 10/2009 | Fraser et al. | 424/76.1 |
| 2011/0311460 | A1 * | 12/2011 | Nguyen et al. | 424/45 |
| 2012/0213711 | A1 * | 8/2012 | Clark et al. | 424/43 |

* cited by examiner

*Primary Examiner* — Charles Boyer

(57) ABSTRACT

An aqueous compressed gas aerosol formulation in combination with a lined steel can, which may also optionally be tin plated, to provide corrosion stability, fragrance stability and color stability. An aerosol formulation of particular advantage for use is an air and/or fabric treatment formulation. The combination provides a compatibility which allows for the ability to use a broader fragrance pallet for the air and/or fabric treatment formulation which is aqueous based in major proportion. The formulation includes, in addition to an aqueous carrier, a fragrance, nonionic surfactant(s) or a blend of nonionic surfactant(s) and cationic surfactant(s), a compressed gas propellant(s), pH adjuster(s), and corrosion inhibitor(s). The formulation has a pH of about 8 to less than 10. The corrosion inhibitor(s) is (are) mild in strength and used in a minor amount.

32 Claims, No Drawings

COMPRESSED GAS AEROSOL COMPOSITION COMPRISING A NON-IONIC SURFACTANT IN A STEEL CAN

RELATED APPLICATION

This application is a continuation of U.S. Ser. No. 13/422,096 filed Mar. 16, 2012, pending.

FIELD OF INVENTION

A compressed gas aerosol formulation is combined with a steel can package under particular parameters for each which are reliant on one another so as to provide an aerosol product having corrosion stability for the steel can, stability for the formulation against discoloration, and fragrance stability against change in scent character. The stability achieved provides for the ability to have a broader fragrance pallet for use and a longer shelf and storage life for the formulation. The aerosol formulation of the invention is in particular directed to compressed gas air and/or fabric treatment, e.g., air or fabric freshening compositions, wherein fragrance is an essential characteristic.

BACKGROUND OF THE INVENTION

Aerosol compositions, including air treatment compositions, are known to be provided in metal cans, such as steel cans. Such compositions generally have a high volatile organic content (VOC) level. In recent years, it has become desirable to reduce in part or whole the VOC of aerosol compositions. As a result, the volatile solvents of the compositions have been replaced in part with water thereby generally giving the aerosol compositions a higher aqueous content. The aqueous content, however, serves to corrode the metal of the cans holding the compositions for storage and dispensing. Steel as used for constructing conventional aerosol cans is often pre-plated with a tin barrier coating in order to protect the underlying steel layer against atmospheric corrosion (rusting). The same tin-plating may also provide protection of the underlying steel layer against corrosion in aqueous environments. The interior of tin-plated steel cans may or may not have an organic coating (lining) or polymeric laminate in order to provide some additional protection of the tin and steel layers against corrosion. It has been found, however, that while tin plating, with or without a lining, initially protects against such corrosion, that the tin plating itself over time may dissolve in aqueous formulations thereby revealing the underlying steel layer. This dissolution of the tin plating into the aqueous formulation serves to degrade the fragrance present and to discolor the formulation. Formula discoloration is essentially a result of reactions between fragrance molecules in aqueous solution at an alkaline pH, i.e., a pH of greater than 7. When the pH is greater than 7, the aqueous system is alkaline/nucleophilic which is an electron-rich system seeking an electron-poor center. The hydroxide ions act either as base-leads to condensation reactions and/or as nucleophile-reactants with electron deficient carbonyl carbon of an ester resulting in ester hydrolysis. Fragrance molecules and ketones containing a carbonyl group, when treated with a base/nucleophile, forms an enolate anion resulting in unsaturated ketones and creates further conjugation in a molecule which absorbs longer wavelengths of UV/visible light producing undesirable discoloration. A steel can can also have traces of iron from either the container or from machining in making the container which can also create a variety of problems resulting in discoloration. Degradation of the fragrance and discoloration of the formulation both affect the functioning of the composition, such as the ability to freshen air with a fragrance of an air freshening composition and the ability to provide a formulation substantially free of discoloration. To combat this failing, combinations of corrosion inhibitors have been incorporated into the aqueous aerosol formulations so as to allow continued use of steel cans, tin-plated steel cans, or other cans subject to corrosion, rather than the more expensive aluminum cans.

One example of a compressed gas aerosol composition in a steel can is disclosed in WO 2011/138620 A1. The aerosol composition includes a borate salt as a corrosion inhibitor. Other corrosion inhibitors include nitrite salts and phosphate salts. Most corrosion inhibitors, however, due to their type of chemistry and the providing of the composition with a more highly alkaline pH (i.e., greater than 9 or 10), detrimentally affect any fragrance present in the composition, both hedonically and color-wise. Color is generally affected by a darkening of the formula and is generally undesirable, for example when the formula becomes darker than a pale yellow since this discoloration generally represents change in structure of the fragrance components which may adversely affect formula stability in terms of color, corrosion and hedonics. A compressed gas aerosol product may be visible on light or white surfaces or soft surfaces due to the larger particle size (fall out) and low evaporation rate. Thus, darkening of the formula may have an undesirable visible result.

Further, steel cans by their nature require a formulation contained therein to be in a certain pH range, generally a pH of 4 to 14, preferably pH of 6 to 12.5, and more preferably a pH of 7 to 9, to avoid general surface rusting and localized forms of corrosion like pitting and crevice corrosion of the steel surface and significant tin-plating dissolution. In view of this and since the pH affects the fragrance stability and coloration of the composition, the pH level also must be addressed.

The above limitations, therefore, greatly affect the fragrance pallet available for use, i.e., the number and types of fragrances compatible for use with the aqueous formulation in a steel can, as well as coloration, which in turn can affect shelf and storage life, as well as consumer acceptance for appropriate hedonics and use on soft surfaces. The invention addresses these disadvantages of the art.

SUMMARY OF THE INVENTION

The compressed gas aerosol (CGA) formulation combined with a steel can package, the package including a liner (such as an organic coating or polymeric laminate) and, optionally tin-plating, on its interior surface provides a unique product which has corrosion stability, color stability, and fragrance stability. This is achieved based on select parameters which rely on each other. A balance between the following parameters provide a stable product as to corrosion inhibition, fragrance stability and product color stability, in particular in an air treatment or fabric and air treatment composition, maintained in a steel can for storage and dispensing wherein the interior surface of the steel can which contacts the composition is tin coated or tin free and covered by a liner (organic coating or polymeric laminate)—(1) corrosion stability depends on the type of corrosion inhibitor used in the composition in conjunction with its concentration and the pH of the formulation in the steel can, (2) concentration of ingredients and pH of the formulation for formula stability, and (3) fragrance hedonic stability depends on interaction of formula components and the fragrance.

For example, although selection of a strong corrosion inhibitor may help to protect against corrosion, a strong corrosion inhibitor can also serve to adversely affect the stability of the fragrance, e.g., borate compounds and highly alkaline materials which can serve as corrosion inhibitors, can also detrimentally react with fragrances to alter their character. Additionally, a higher pH (above 9), while helpful in protecting against steel corrosion, can also affect adversely on fragrance and formulation stability, e.g., the formulation juice discolors and the character of the fragrance changes. However, a particular combination of parameters have provided unexpected results, i.e., the particular combination of parameters providing fragrance formulation and color stability, and the availability of a large fragrance pallet instead of a fragrance pallet having only a limited number of fragrances from which to choose.

Formulation and container compatibility is provided by the invention based on a combination of a steel can having on its interior surfaces, at least those surfaces which are in contact with the stored composition, a liner which may be an organic coating or polymeric laminate, or tin plating (a tin coating) with a liner over top of the tin plating, and a formulation including one or more surfactants wherein the surfactant is at least one nonionic surfactant or is a blend of at least one nonionic surfactant and at least one cationic surfactant; at least one compressed gas propellant, at least one corrosion inhibitor, at least one pH adjuster, optionally at least one solvent wherein the solvent is an alcohol and/or glycol compound, optionally at least one buffer, and optionally at least one preservative, wherein the formulation has a pH in the range of about 8 to less than 10, preferably 8.5 to 9.5. Commercially, aerosol compositions for treating air or fabric which are a single phase aerosol formulation often have a volatile organic content (VOC) of up to 30%, or higher. The formulations of the invention preferably have a VOC of 0 to 6%, more preferably a VOC in a range of 0.5% to 5.5%, even more preferably have a VOC as low as less than or equal to 0.1% and is most preferably 0%. When the VOC level of the formulations of the invention are referred to herein, it is to be understood that such VOC percentage does not include the VOC of the fragrance component of the formulation which may have a combined VOC of up to 2%. "Fragrance or "fragrance component" as used herein is to be understood to include a substance or mixture of substances of aroma chemicals, natural essential oils, or other functional components with a combined vapor pressure not in excess of 2 mm of Hg at 20° C. and having as a sole purpose the imparting of an odor or scent, or to counteract a malodor.

The compressed gas propellant can be oxygen or non-oxygen containing. Preferably, however, the compressed gas propellant is non-oxygen-containing, such as nitrogen or argon, since the presence of oxygen (such as in air) can increase the likelihood of corrosion and corrosion reactions. Corrosion/corrosion reactions and other oxidation reactions also influence fragrance stability. For example, dissolved oxygen not removed during manufacturing may be present in the liquid phase of a product which can act to oxidize or destabilize formula components. Accordingly, non-oxygen containing or inert compressed gases provide for further increased stability in such situations.

DETAILED DESCRIPTION OF THE INVENTION

The invention provides a compatible combination of an aqueous compressed gas formulation and a steel can having a lining therein, and optionally tin plating, to provide an aerosol product. Particularly suitable for use in the combination as the aqueous compressed gas formulation is an air and/or fabric treatment formulation as set forth in the description herein. The air and/or fabric treatment formulation includes a fragrance which is stable as to its character (scent) and the formulation remains stable as to its coloration. Due to the pH range and the compatibility between the container and the formulation, greater flexibility in the fragrance ingredients is available thereby providing a broad fragrance pallet, i.e., number and type of scents, for incorporation into the formulation. Further, corrosion inhibitors included in the formulation can be milder in strength and used in a lesser amount as compared to that required in the absence of the inventive combination. More particularly, the alkalinity (pH) of the formulations of the invention, selection of ingredients and their concentrations, do not facilitate some of the nucleophilic type chemical reactions between fragrance molecules as with certain conventional systems, for example a formula including a multi-purpose corrosion inhibitor/pH adjusting agent/buffering agent sodium borate, having a pKa of 9.2, facilitates some aggressive reactions with fragrance compositions, as well as provides a higher pH. The combination or system of the invention provides for corrosion stability, formulation stability, color stability and fragrance stability in compressed gas aerosol aqueous-based air and/or fabric treatment compositions. The high aqueous content of the formulation traditionally results in corrosion of the steel can container. To combat this corrosion, typically high strength (based on nature and/or amount) corrosion inhibitor(s) are present in an air or fabric treatment formulation, which in turn results in a high pH for the formulation, e.g., greater than 9 or 10 in the case of a borate. This severely limits the number and nature of fragrances available for inclusion in the formulation based on the type/amount of corrosion inhibitor and the highly alkaline pH. The present invention overcomes these disadvantages.

Steel cans with a liner, either free of tin plating (tin coating) or being tin plated, suitable for use in dispensing an aerosol composition of the combination of the invention are as commercially available, for example, from Crown Cork & Seal, Ball Corporation, Bway, DS Container, Sexton Can, Colep, Simsek, Impress & Sarten; Inesa, Comeca; Huata & Cofco, MMI, Metcan, Swan, Canpac and Aestar. The steel cans are structured for dispensing an aerosol composition and include a dispensing top, a body and a base wall. The interior surfaces of the steel cans include thereon a liner alone or also are coated with tin. The cans are preferably three piece steel cans, but can also be two piece steel cans.

The interior surfaces of the steel cans are preferably lined with an organic coating or polymeric laminate, and when optionally also tin plated (coated), the lining is present over top of the tin plating. The polymeric lining can be composed of materials with different chemistry known for use as interior coatings on a metal surface, such as epoxy-urea, epoxy, epoxy-phenol, vinyl, amide-imides, acrylic, epoxy-vinyl, alkyd and the like. A preferred lining material is epoxy-urea, such as commercially available under the tradename VALSPAR 20S55 as manufactured by Valspar. The lining will have a thickness in a range of from about 1 micron to about 12 microns or greater.

The formulation included in the steel can for dispersing as a aerosol is preferably a compressed gas propellant system. Compressed gas aerosols generally have a higher particle size, for example in a range of about 30 μm to about 200 μm (μm=micrometers=microns) on average and, accordingly, can have a higher particle fall out as compared to liquefied petroleum gas (LPG) aerosols. Thus, when a compressed gas formulation is not stable resulting in discoloration of the formulation, the particle fallout can be more visible to a user, especially on white or light colored surfaces, as well as on soft surfaces such as fabric. Stable compressed gas formulations are clear or light in color. Unstable compressed gas formulations discolor to a deep yellow to brown liquid and, thus, can discolor the surface on which the formulation particles land during fallout.

In conjunction with the lined, and optionally tin plated, steel can, the air and/or fabric treatment formulation will have a predetermined pH; defined surfactants; and particular concentration of corrosion inhibitor, which is lesser in amount as compared to corrosion inhibitors as used in conventional compressed gas aerosols. The stability of the compressed gas formulation achieved allows for a wide scope in number and characteristics of fragrances which are useful in the formulation. Fragrance and color stability is achieved for an extended amount of time as compared to formulations having high alkaline pHs or strong corrosion inhibitors (either by nature or amount/number of corrosion inhibitors present).

As to the air or fabric treatment formulation, such is generally preferred as set forth in Table 1 below.

TABLE 1

| Ingredients | Wt.% Range |
| --- | --- |
| Water | about 80 to about 99 |
| Surfactant(s) | about 0.5 to about 2.0 |
| Fragrance(s) | about 0.1 to about 2 |
| Compressed Gas Propellant(s) | about 0.5 to about 2 |
| pH Adjuster(s) | Sufficient to achieve pH of about 8 to less than 10 |
| Corrosion Inhibitor(s) | about 0.01 to about 0.5 |
| Non-Water Solvent(s) | 0 to about 6.0 |
| Buffer(s) | 0 to about 0.5 |
| Preservative(s) | 0 to about 1.0 |

Weight percent (wt. %) of the total composition in Table 1 and as used in the description and claims is based on 100 wt. %. The ingredient wt. % given is based on the wt. % of the whole ingredient and not simply on the active(s) of the ingredient.

The water component is a carrier solvent and can be deionized water, reverse osmosis water, distilled water, tap water, and/or the like. Preferred are deionized water and reverse osmosis water. Generally, water is present in an amount greater than about 80 wt. % but less than 100 wt. %. The preferred amount of water present is as set forth in Table 1 above. More preferably, water is present in an amount of about 90 to about 99 wt. %, and most preferably in an amount of about 92 to about 97.5 wt. %.

Surfactants suitable for inclusion in the formulation are limited to nonionic surfactants or a blend of nonionic and cationic surfactants. Cationic surfactant(s) alone are not sufficient in the formulations of the invention for achieving the advantages described herein. Anionic, amphoteric and zwitterionic surfactants are excluded from use in the compressed gas air treatment formulations of the invention. Such surfactants have a more corrosive effect. The surfactant component can be one or more surfactants and can include at least one nonionic surfactant, or a blend of at least one nonionic surfactant and at least one cationic surfactant.

Suitable nonionic surfactants useful in the air treatment formulation include, but are not limited to, polyalkoxylated hydrogenated castor oil, preferably polyethoxylated hydrogenated caster oil such as TAGAT CH60 (60 ethylene oxide (EO) units), TAGAT CH40 (40 EO units); hydrogenated and ethoxylated castor oil blends, e.g. EUMULGIN HPS (40 EO units); secondary alcohol ethoxylates, e.g., TERGITOL brand surfactants such as TERGITOL 15-S-12 and TERGITOL 15-S-7; ethoxylated linear alcohols, e.g., LUTENSOL brand such as LUTENSOL A08 (8 EO units); sorbitan monooleate; polyethylene sorbitan monooleate; polyoxyethylene sorbitan monolaurate; alkyl polyglycosides; polyethyleneoxide/polypropyleneoxide; alkyl phenol ethoxylated carboxylated alcohols; and mixtures thereof.

The at least one nonionic surfactant is present in an amount range preferably as set forth in Table 1, i.e., in a range of about 0.5 to about 2.0 wt. %, and more preferably in a range of about 0.5 to about 1.0 wt. %, and most preferably about 0.5 to about 0.8 wt. %.

Cationic surfactants suitable for inclusion in the compressed gas air treatment formulation include, but are not limited to, the following: quaternary ammonium salts, polyoxyethylene alkyl, alicyclic amines, and mixtures thereof.

The at least one cationic surfactant is present in an amount range of preferably 0 to about 3.0 wt. %, and more preferably present in an amount of 0 to about 1.0 wt. %. As set forth above, the cationic surfactant is used in combination with a nonionic surfactant and not as the sole surfactant.

Fragrance(s) suitable for inclusion in the compressed gas air and/or fabric treatment formulation can be a natural or synthetic fragrance, based on a single component or a blend of components. Fragrances are commercially available from various fragrance manufacturers, such as Takasago, International Flavors and Fragrances, Inc., Quest, Firmenich, Givaudan, Symrise, and the like.

The fragrance(s) is (are) present in an amount range generally as set forth above in Table 1 and is (are) preferably present in a range of about 0.1 to about 2.0 wt. %, and more preferably present in a range of from about 0.3 to about 1.0 wt. %.

The compressed gas propellant may be any suitable conventionally known compressed gas propellant, either oxygen or non-oxygen containing, including, but not limited to, nitrogen, argon, methane, ethane, air, nitrous oxide, carbon dioxide, or mixtures thereof. Preferred compressed gas propellants for use are inert and do not contain oxygen. The presence of oxygen, such as in air, increases the chance of corrosion and corrosion reactions. Further, oxidation reactions influence fragrance stability. So while there is no limitation on the compressed air propellant, it is preferred that the compressed gas propellant is an inert medium, and does not include oxygen therein.

The compressed gas propellant is present in an amount generally as set forth above in Table 1, i.e., is preferably present in a range of about 0.5 to about 2.0 wt. %, and more preferably in a range of about 0.5 to about 1.0 wt. %. The compressed gas propellant is pressurized in a range of from about 120 to about 160 psig, preferably from about 130 to about 150 psig, and more preferably from about 132 to about 142 psig.

Corrosion inhibitor(s) suitable for inclusion in the compressed gas air treatment formulation is (are), but not limited to, phosphates, such as potassium dihydrogen phosphate, potassium hydrogen phosphate, diammonium phosphate, potassium phosphate (monobasic or dibasic), sodium phosphate (monobasic or dibasic); nitrites, such as sodium nitrite, potassium nitrite, and ammonium nitrite; aminomethyl propanol; and/or silicates, such as sodium meta-silicate.

The corrosion inhibitor(s) is (are) present in the general amount as set forth above in Table 1, and is (are) preferably present in a range of about 0.01 to about 0.5 wt. %, and more preferably in a range of about 0.1 to about 0.4 wt. %.

Non-water solvents suitable for use include alcohols and glycols only. Examples of alcohol and glycol non-water solvents suitable for use include, but are not limited to, alkylene glycols, such as propylene glycol and triethylene glycol; and lower carbon chain (e.g., C2 to C5) alcohols, such as ethanol and propanol.

The non-water solvent(s) is (are) present in an amount as set forth above in Table 1, i.e., preferably is present in a range of 0 to about 6.0 wt. %, and more preferably in a range of about 0.1 to about 5.0 wt. %. Most preferably, the non-water solvent is present in an amount of less than or equal to 0.1 wt. % so that the formulation has a low or no VOC.

Compounds suitable for inclusion in the compressed gas air and/or fabric treatment formulation as pH adjusters or controllers include, but are not limited to, carbonates, such as sodium carbonate; silicates, such as sodium meta-silicate pentahydrate (which may provide a dual function as a pH adjuster and corrosion inhibitor); phosphates, such as disodium phosphate, and dipotassium phosphate; hydroxides, such as sodium hydroxide; ammonium hydroxide; THAM-Tris-(hydroxymethyl) aminoethane; 2-amino-2-methyl-propane diol; and the like.

The pH adjuster is used in a sufficient amount suitable to obtain the desired pH in a range of about 8 to less than 10, preferably a pH range of about 8.5 to about 9.5, and more preferably a pH range of about 8.5 to about 9.0.

Buffer compound(s) suitable for inclusion in the compressed gas air treatment formulation includes, but is not limited to, bicarbonates, such as sodium bicarbonate; phosphates; ammonium hydroxide; THAM-Tris (hydroxymethyl) aminoethane; 2-amino-2-methyl-propane diol; and the like. It is noted that some well known pH buffering agents, such as phosphates, carbonates, ammonium hydroxide, THAM-Tris (hydroxymethyl) aminoethane, and 2-amino-2-methyl-propane diol, will provide a multi-purpose function of corrosion inhibitor, pH adjustor, and buffering agent. In such instance, one or a combination of ingredients may be used to meet these functions and amounts thereof adjusted accordingly within the scope of the invention.

The buffer(s) is (are) present in an amount as generally set forth in Table 1 above, and preferably in a range of about 0.01 to about 0.5 wt. %, and more preferably in a range of about 0.1 to about 0.4 wt. %.

Preservative(s) suitable for inclusion in the compressed gas air treatment formulation include, but are not limited to isothiazolinones, such as 1,2,-benzisothiazole-3(2H)-one and 2-methylisothiazole-3(2H)-one, which is sold as a blend under the trade name ACTICIDE MB; 2-methyl-4-isothiazolin-3-one, which is sold under the trade name NEOLONE M-10; and 2-methyl-2H-isothiazol-3-one and 3-iodo-2-propynyl-butyl carbamate, which is sold as a blend under the trade name ACTICIDE IM.

The preservative(s) is (are) present in an amount as generally set forth above in Table 1, preferably in an amount in the range of about 0.01 to about 1.0 wt. %, more preferably in a range of about 0.01 to about 0.5 wt. %, and most preferably in a range of about 0.05 to about 0.2 wt. %.

The concentrations of the corrosion inhibitor component, pH adjuster component and, if present, the buffer component and preservative component in combination contribute to the benefits achieved in the present invention, in particular in that these components are able to serve their functions while being present in minor amounts. This serves to increase stability as to the fragrance and color of the formulation, since disadvantageous interaction or breakdown is less likely. Adjuvants as conventionally known in the art can be included as desired so long as they necessarily do not disrupt the fulfillment of the formulation/container advantages as described herein. The total elemental phosphate level in the formulation is 0.05% (per can of 227 μm fill weight).

Set forth below are examples of the compressed gas air treatment formulation of the invention.

| Ingredients | Example 1 Wt. % | Example 2 Wt. % | Example 3 Wt. % | Example 4 Wt. % |
|---|---|---|---|---|
| Reverse Osmosis/ Deionized Water (Solvent) | 97.227 | 97.152 | 92.283 | 97.075 |
| Sodium Bicarbonate (Buffer) | 0.185 | — | 0.185 | — |
| Sodium Carbonate (pH Adjuster) | 0.016 | 0.181 | — | 0.181 |
| Sodium Nitrite (Corrosion Inhibitor) | 0.1 | — | 0.05 | — |
| Hydrogenated Castor Oil 60 Ethoxylate (Nonionic Surfactant) (TAGAT CH 60) | 0.469 | 0.469 | 0.469 | 0.469 |
| Alkyloxypoly-ethyleneoxyethanol (Nonionic Surfactant) (TERGITOL 15-S-7) | 0.281 | 0.281 | 0.281 | 0.281 |
| Fragrance | 0.5 | 0.5 | 0.5 | 0.5 |
| Propylene Glycol, Industrial Grade (Solvent) | 0.469 | 0.469 | 0.469 | 0.469 |
| 1,2-Benzisothiazole-3(2H)-one (<2.5%) and 2-Methylisothiazole-3(2H)-one (<2.5%) (Preservative) (ACTICIDE MB) | 0.075 | 0.075 | 0.075 | 0.050 |
| Nitrogen Gas (Propellant) | 0.678 | 0.678 | 0.678 | 0.678 |
| Sodium Dihydrogen Phosphate (Corrosion Inhibitor) | — | 0.195 | — | 0.195 |
| Sodium Meta-Silicate Pentahydrate (pH Adjuster) | — | — | 0.01 | — |
| Ethyl Alcohol (Solvent) | — | — | 5.0 | — |
| N,N-Dialkyl-N,N-Dimethyl Ammonium Chloride | — | — | — | 0.102 |
| | 100% | 100% | 100% | 100% |

The formulations in each of Examples 1-4 were contained in a 3-piece tin plated steel can lined with VALSPAR 20S55 which is of an epoxy-urea lining.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention and are embraced by the appended claims.

It is claimed:

1. An aerosol system comprising:

(a) a spray dispenser in combination with (b) an aqueous-based product contained in said dispenser for dispensing therefrom, wherein said spray dispenser comprises:

(i) a spray head adapted to dispense said product and
(ii) a steel container including an interior for holding said product, wherein walls forming said interior in contact with said product have a lining thereon, said lining being an organic coating or a polymeric laminate;
wherein said product comprises
(1) about 0.5 to about 2 wt. % of nonionic surfactant,
(2) a cationic surfactant present and in an amount up to about 3 wt. %,
(3) about 0.1 to about 2 wt. % of a fragrance component,
(4) about 0.5 to about 2 wt. % of compressed gas propellant,
(5) pH adjuster in an amount to achieve a pH of about 8 to less than 10 for the product,
(6) about 0.01 to about 0.5 wt. % of corrosion inhibitor, and
(7) about 80 to less than 100 wt. % water;
  wherein components (1) to (7) of the product are present in amounts which in combination with the lining in the steel container provide said product as visually clear or substantially non-colored to an extent not to discolor a surface which the product contacts upon dispensing; and
wherein anionic, amphoteric and zwitterionic surfactants are excluded from the system.

2. An aerosol product comprising in combination
(a) steel can with aerosol dispensing top, body and base, wherein said steel can has an interior surface having thereon a lining which is an organic coating or polymeric laminate, and, optionally a tin coating, wherein when the tin coating is present, the lining is provided over top of said tin coating; and
(b) a composition consisting of
  (i) water in an amount greater than about 80 wt. % but less than 100 wt. %,
  (ii) about 0.5 to about 2 wt. % of compressed gas propellant,
  (iii) about 0.1 to about 2 wt. % of fragrance component,
  (iv) pH adjuster component in an amount sufficient to provide said composition with a pH of about 8 to less than 10,
  (v) corrosion inhibitor component in an amount greater than 0, but equal to or less than about 0.5 wt. % comprising one or more of a phosphate, nitrite or silicate corrosion inhibiting compound,
  (vi) about 0.5 to about 2 wt. % of surfactant component which is either (1) at least one nonionic surfactant or (2) a blend of at least one nonionic surfactant and at least one cationic surfactant,
  (vii) optionally a solvent selected from a group consisting of alcohols and glycols,
  (viii) optionally a buffer component, and
  (ix) optionally a preservative component;
wherein said composition is contained in said steel can and contacts said lining on said interior surface of said steel can;
wherein said composition excludes anionic, amphoteric and zwitterionic surfactants.

3. The system of claim 1, wherein said product consists of
(i) about 80 to about 99 wt. % of said water;
(ii) about 0.5 to about 2 wt. % of said compressed gas propellant;
(iii) about 0.1 to about 2 wt. % of said fragrance component;
(iv) said pH adjuster in an amount sufficient to provide said composition with a pH of about 8 to about 9.5;
(v) about 0.01 to about 0.5 wt. % of said corrosion inhibitor;
(vi) about 0.5 to about 2 wt. % of said nonionic surfactant alone or in combination with said cationic surfactant;

(vii) about 0.1 to about 6 wt. % of solvent;
(viii) about 0.01 to about 0.5 wt. % of buffer, and
(ix) about 0.01 to about 1.0 wt. % of preservative.

4. The system of claim 1 wherein said pH is about 8.5 to about 9.5.
5. The system of claim 1 wherein said VOC is in a range of 0.1% to 5.5%.
6. The product of claim 2 wherein said VOC is in a range of 0.1% to 5.5%.
7. The system of claim 1 wherein said VOC is equal to or less than 0.1%.
8. The product of claim 2 wherein said VOC is equal to or less than 0.1%.
9. The system of claim 1 wherein said lining comprises epoxy-urea.
10. The product of claim 2 wherein said lining comprises epoxy-urea.
11. The system of claim 1 wherein said lining comprises epoxy or epoxy-phenol or vinyl or an amide-imide.
12. The product of claim 2 wherein said lining comprises epoxy or epoxy-phenol or vinyl or an amide-imide.
13. The system of claim 1 wherein said compressed gas propellant is selected from a group consisting of nitrogen, argon, air, nitrous oxide, carbon dioxide, methane, ethane or mixtures thereof.
14. The product of claim 2 wherein said compressed gas propellant is selected from a group consisting of nitrogen, argon, air, nitrous oxide, carbon dioxide, methane, ethane or mixtures thereof.
15. The system of claim 1 wherein said compressed gas propellant is nitrogen or argon.
16. The product of claim 2 wherein said compressed gas propellant is nitrogen or argon.
17. The system of claim 1 wherein said nonionic surfactant is one or more secondary alkoxylated alcohol and/or polyalkoxylated hydrogenated castor oil.
18. The system of claim 3 wherein the buffer is an alkali metal bicarbonate or a phosphate.
19. The system of claim 3 wherein the solvent is selected from the group consisting of alcohols and glycols.
20. The system of claim 3 wherein the solvent is propylene glycol.
21. An aerosol system comprising:
(a) a spray dispenser in combination with
(b) an aqueous-based product contained in said dispenser for dispensing therefrom;
wherein said spray dispenser comprises:
(i) a spray head adapted to dispense said product and
(ii) a steel container including an interior for holding said product, wherein walls forming said interior in contact with said product have a lining thereon, said lining being an organic coating or a polymeric laminate;
wherein said product consists of:
(1) about 0.5 to about 2 wt. % of nonionic surfactant,
(2) 0 to about 3 wt. % of cationic surfactant,
(3) about 0.1 to about 2 wt. % of a fragrance component,
(4) about 0.5 to about 2 wt. % of compressed gas propellant,
(5) pH adjuster in an amount to achieve a pH of about 8 to less than 10 for the product,
(6) about 0.01 to about 0.5 wt. % of corrosion inhibitor,
(7) about 80 to less than 100 wt. % water;
(8) optionally a solvent selected from the group consisting of alcohols and glycols;
(9) optionally a buffer component; and
(10) optionally a preservative component;
  wherein components (1) to (10) of the product are present in amounts which in combination with the lining in the steel container provide said product as visually clear or substantially non-colored to an extent not to discolor a surface which the product contacts upon dispensing; and wherein anionic, amphoteric and zwitterionic surfactants are excluded from the system.

22. The system of claim 21, wherein said product consists of
(i) about 80 to about 99 wt. % of said water;
(ii) about 0.5 to about 2 wt. % of said compressed gas propellant;
(iii) about 0.1 to about 2 wt. % of said fragrance component;
(iv) said pH adjuster in an amount sufficient to provide said composition with a pH of about 8 to about 9.5;
(v) about 0.01 to about 0.5 wt. % of said corrosion inhibitor;
(vi) about 0.5 to about 2 wt. % of said nonionic surfactant alone or in combination with said cationic surfactant;
(vii) about 0.1 to about 6 wt. % of solvent;
(viii) about 0.01 to about 0.5 wt. % of buffer, and
(ix) about 0.01 to about 1.0 wt. % of preservative.

23. The system of claim 21 wherein said pH is about 8.5 to about 9.5.

24. The system of claim 21 wherein said VOC is in a range of 0.1% to 5.5%.

25. The system of claim 21 wherein said VOC is equal to or less than 0.1%.

26. The system of claim 21 wherein said lining comprises epoxy-urea.

27. The system of claim 21 wherein said lining comprises epoxy or epoxy-phenol or vinyl or an amide-imide.

28. The system of claim 21 wherein said compressed gas propellant is selected from the group consisting of nitrogen, argon, air, nitrous oxide, carbon dioxide, methane, ethane or mixtures thereof.

29. The system of claim 21 wherein said compressed gas propellant is nitrogen or argon.

30. The system of claim 21 wherein said nonionic surfactant is one or more secondary alkoxylated alcohol and/or polyalkoxylated hydrogenated castor oil.

31. The system of claim 21 wherein the buffer is present and is an alkali metal bicarbonate or a phosphate.

32. The system of claim 21 wherein the solvent is present and is propylene glycol.

* * * * *